US 8,876,293 B2

(12) United States Patent
Gierhart et al.

(10) Patent No.: US 8,876,293 B2
(45) Date of Patent: Nov. 4, 2014

(54) MACULAR PIGMENT MEASUREMENT DEVICE WITH DATA QUALITY INDEXING FEATURE

(71) Applicant: ZeaVision, LLC, Chesterfield, MO (US)

(72) Inventors: Dennis L. Gierhart, Chesterfield, MO (US); Christopher Gerald Barber, Chesterfield, MO (US); Malcolm Stuart Grover, Stuart, FL (US)

(73) Assignee: ZeaVision, LLC, Chesterfield, MO (US)

( * ) Notice: Subject to any disclaimer, the term of this patent is extended or adjusted under 35 U.S.C. 154(b) by 0 days.

(21) Appl. No.: 13/791,145

(22) Filed: Mar. 8, 2013

(65) Prior Publication Data

US 2014/0118698 A1    May 1, 2014

Related U.S. Application Data

(60) Provisional application No. 61/720,737, filed on Oct. 31, 2012.

(51) Int. Cl.
*A61B 3/02* (2006.01)
*A61B 3/00* (2006.01)

(52) U.S. Cl.
USPC .......................................... 351/222; 351/246

(58) Field of Classification Search
USPC ................................................ 351/200–246
See application file for complete search history.

(56) References Cited

U.S. PATENT DOCUMENTS

| | | | |
|---|---|---|---|
| 4,861,154 A | 8/1989 | Sherwin et al. | |
| 4,889,422 A | 12/1989 | Pavlidis | |
| 5,331,969 A | 7/1994 | Silberstein | |
| 6,315,412 B1 * | 11/2001 | Snodderly et al. | 351/200 |
| RE38,009 E | 2/2003 | Garnett et al. | |
| 6,572,229 B2 | 6/2003 | Wei | |
| 6,578,965 B2 | 6/2003 | Grant | |
| 6,623,117 B2 | 9/2003 | Shibutani et al. | |
| 6,688,744 B2 | 2/2004 | Wei et al. | |
| 6,729,728 B2 | 5/2004 | Wei et al. | |
| 6,834,958 B2 | 12/2004 | Cornsweet et al. | |
| 6,969,856 B1 | 11/2005 | Hillenbrand et al. | |

(Continued)

FOREIGN PATENT DOCUMENTS

WO    2007/127134    11/2007

OTHER PUBLICATIONS

Product Brochure: QuantifEye® Macular Pigment Optical Density Measurement (MPOD). ZeaVision LLC. Mar. 2010 (2 pages).

(Continued)

*Primary Examiner* — Mohammed Hasan
(74) *Attorney, Agent, or Firm* — Nixon Peabody LLP (57) ABSTRACT

A system measures macular pigment of a macula of a human eye of a subject. The system comprises a light source having a first light and a second light that modulate at variable frequencies, an input device for receiving an input indicating the frequency at which the user perceives the modulation of the first light and a second light, a display device, at least one processor, and one or more memory devices. The one or more memory devices storing instructions that, when executed by at least one processor, cause the system to (i) display, on the display device, test data corresponding to the user's inputs from the input device, (ii) determine whether the test data are valid or invalid through a curve-fitting algorithm, (iii) automatically indicate that the test data are valid or invalid.

18 Claims, 4 Drawing Sheets

(56) References Cited

U.S. PATENT DOCUMENTS

| | | | |
|---|---|---|---|
| 7,156,518 B2 | 1/2007 | Cornsweet et al. | |
| 7,331,669 B2* | 2/2008 | Elsner | 351/206 |
| 7,390,090 B2* | 6/2008 | Murray et al. | 351/237 |
| 7,441,896 B2* | 10/2008 | Bone et al. | 351/213 |
| 7,467,870 B2 | 12/2008 | van de Kraats et al. | |
| 8,408,702 B2 | 4/2013 | Gierhart et al. | |
| 8,485,664 B2 | 7/2013 | Rowe | |
| 2003/0130579 A1 | 7/2003 | McClane et al. | |
| 2004/0081628 A1 | 4/2004 | Gierhart et al. | |
| 2004/0193068 A1 | 9/2004 | Burton et al. | 600/544 |
| 2004/0207811 A1 | 10/2004 | Elsner | |
| 2005/0110949 A1 | 5/2005 | Goldfain et al. | |
| 2005/0147648 A1 | 7/2005 | Gierhart | |
| 2005/0171212 A1 | 8/2005 | Gierhart | |
| 2006/0039954 A1 | 2/2006 | Gierhart et al. | |
| 2006/0089411 A1 | 4/2006 | Gierhart | |
| 2006/0227290 A1 | 10/2006 | Murray et al. | 351/243 |
| 2006/0270739 A1 | 11/2006 | Johnson et al. | 514/560 |
| 2007/0082066 A1 | 4/2007 | Gierhart et al. | |
| 2007/0252950 A1 | 11/2007 | Kraats et al. | |
| 2010/0097573 A1 | 4/2010 | Verdooner et al. | |
| 2010/0241450 A1 | 9/2010 | Gierhart et al. | |
| 2012/0257164 A1 | 10/2012 | Zee et al. | 351/206 |

OTHER PUBLICATIONS

"Effect of wavelength on in vivo images of the human cone mosaic", Stacey S. Choi, Nathan Doble, Julianna Lin, Julian Christou, David R. Williams, Journal of the Optical Society of America, vol. 22, 12, Dec. 2005 (8 pages).

"Fast and Objective Measurement of Macular Pigment With Natural Pupil" (Dirk van Norren, Jan van de Kraats, Suze Valen & Tos T.J.M. Berendschot) Apr. 30, 2005—(1-page).

"Fundus Photography For Measurement Of Macular Pigment Density Distribution in Children" (Lo J. Bour, Lily Koo, Francois C. Delort, Patricia Apkarian, Anne B. Fulton) Investigative Ophthalmology & Visual Science, May 2002, vol. 43, No. 5 Copyright © Association for Research in Vision and Ophthalmology—(6-pages).

"Comparison Of Fundus Autofluorescence and Minimum-Motion Measurements Of Macular Pigment Distribution Profiles Derived From Identical Retinal Areas" Anthony G. Robson, Glen Harding, Frederick W. Fitzke, Jack D. Moreland "Perception" vol. 34 2005—www.perceptionweb.com—(7 pages), December.

"Macular Pigment Assessment By Motion Photometry" Moreland JD.—MacKay Institute, Keele University, Staffordshire, ST5 5BG, UK. j.d.moreland@cns.keele.ac.uk PubMed—Arch Biochem Biophys. Oct. 15, 2004; 430(2):143-8—(6 pages).

"Macular Pigment Optical Density Measurement: A Novel Compact Instrument" Stephen Beatty, Hui-Hiang Koh, David Carden and Ian J. Murray, Ophthal. Physical Opt. vol. 20, No. 2, pp. 105-111, 2000 © 2000 The College of Optometrists, Published by Elsevier Science Ltd. Printed in Great Britain—(7-pages), November.

"A Practical Method For Measuring Macular Pigment Optical Density" Billy R. Wooten, Billy R. Hammond, Jr., Richard I. Land and D. Max Snodderly Investigation Ophthalmology and Visual Science. 1999;40:2481-2489. © 1999 by The Association For Research In Vision and Ophthalmology, Inc. (14 pages), October.

"Macular Pigment Measurement By Heterochromatic Flicker Photometry In Order Subjects: The Carotenoids And Age-Related Eye Disease Study" D. Max Snodderly, Julie A. Mares, Billy R. Wooten, Lisa Oxton, Michael Gruber, and Tara Ficek, for the AREDS Macular Pigment Study Group Investigative Ophthalmology & Visual Science, Feb. 2004, vol. 45, No. 2 Copyright © Association for Research in Vision and Ophthalmology.-(8-pages).

"Macular Pigment" Property of the University of Westminster, Vision Research Group John Mellerio—mellerj@wmin.ac.uk—(10 pages), Feb. 2004.

"Heterochromatic Flicker Photometry" Department of Physics, Florida International University, Miami 33199, USA Bone RA, Landrum JT.—bone@fiu.edu PubMed—Arch Biochem Biophys. Oct. 15, 2004; 430(2):137-42—(6 pages).

"A Portable Instrument For Measuring Macular Pigment With Central Fixation" Mellerio J, Ahmadi-Lari S, van Kuijk F, Pauleikhoff D, Bird A, Marshall J. (11 pages), Oct. 2004.

"Macular Pigment Density Measured By Autofluorescence Spectrometry: Comparison with Reflectometry and Heterochromatic Flicker Photometry" Delori FC, Goger DG, Hammond BR, Snodderly DM, Burns SA. Schepens Eye Research Institute, Boston, Massachusetts 02114, USA. PubMed—Opt Soc Am A Opt Image Sci Vis. Jun. 2001;18(6):1212-30.—(19 pages).

"Autofluorescence Method To Measure Macular Pigment Optical Densities Fluorometry And Autofluorescence Imaging" Francois C. Delori Schepens Eye Research Institute and Harvard Medical School, Boston, M.A. USA © 2004 Published by Elsevier Inc.—(7 pages), December.

"Resonance Raman Measurement of Macular Carotenoids In The Living Human Eye" Paul S. Bernstein, Da-You Zhao, Mohsen Sharifzadeh, Igor V. Ermakov, Werner Gellermann Department of Ophthalmology and Visual Sciences, Moran Eye Center, University of Utah School of Medicine, Salt Lake City, UT, USA, Department of Physics, University of Utah, Salt Lake City, UT © 2004 Elsevier Inc.—(7 pages), October.

"Influence of Lutein Supplementation On Macular Pigment, Assessed with Two Objective Techniques" Tos T. J. M. Berendschot[1], R. Alexandra Goldbohm[2], Wilhelmina A.A. Klöpping[2], Jan van de Kraats[1], Jeannette van Norel[1], and Dirk van Norren [1] © 2000 by The Association for Research in Vision and Ophthalmology, Inc.—(1 page), October.

"Influence Of Lutein Supplementation On Macular Pigment, Assessed With Two Objective Techniques" Berendschot TT, Goldbohm RA, Klopping WA, van de Kraats J, van Norel J, van Norren D. University Medical Centre Utrecht, Department of Ophthalmology, The Netherlands PubMed—Invest Ophthal. Vis. Sci. Oct. 2000; 41(11):3322-6.—(5 pages).

"Objective Determination Of The Macular Pigment Optical Density Using Fundus Reflectance Spectroscopy" Tos T.J.M. Berendschot and Dirk van Norren Department of Ophthalmology, University Medical Center Utrecht, The Netherlands © 2004 Elsevier, Inc.—(7 pages), April.

"Current Concepts In The Pathogenesis Of Age-Related Macular Degeneration" Marco A. Zarbin, MD, PhD. Arch Ophthalmol./vol. 122. Apr. 2004—www.archophthalmol.com © 2004 American Medical Association.—(17 pages).

"Assessment Of The Validity Of In Vivo Methods Of Measuring Human Macular Pigment Optical Density" Hammond BR Jr., Wooten BR, Smollon B. Vision Science Laboratory, University Of Georgia, Athens, Georgia 30602-3013, USA PubMed—Optom Vis. Sci. May 2005; 82(5):387-404—(17 pages).

In Vivo Assessment Of Retinal Carotenoids: Macular Pigment Detection Techniques and Their Impact On Monitoring Pigment Status Joanne Curran Celentano, Joanne D. Burke and Billy R Hammond, Jr. Department of Animal and Nutritional Sciences, University of New Hampshire, Durham, NH and Department of Psychology and Behavior Sciences, University of Georgia, Athens, GA © 2002 American Society for Nutritional Sciences—(5 pages), December.

"Macular Degeneration—The Latest Scientific Discoveries and Treatments For Preserving Your Sight" Robert D'Amato, M.D., Ph.D., and John Snyder Copyright © 2000 by Robert d'Amato and Joan Snyder—(2 pages), June.

"Age-Related Macular Degeneration" Jeffrey W. Berger, Stuart L. Fine and Maureen G. Maguire, Mosby, 1999.Jul. 2002 / 576 pp, illus. /ISBN: 08247-0682-X—(3-pages.).

"The pathways of light measured in fundus reflectometry," J. van. de. Kraats, T.T.J.M. Berendschot, and D.van Norren, 1996, Vision Res. 36 (19 pages), October.

"Spectral reflectance of the human ocular fundus," F.C. Delori and K.P. Pfibsen, 1989, Appl. Opt. 28 (18 pages), October.

"Visible and near infrared light absorption in pigment epithelium and choriod," V.P. Gabel, R. Birngruber, and F. Hillenkamp, *Excerpta Medica, International Congress Series* No. 450, K. Shimizu and J.A. Oosterhuis, eds, (Elsevier, Amsterdam, 1978) (4 pages), November.

(56) References Cited

OTHER PUBLICATIONS

"Biological control of primate macular pigment. Biochemical and densitometric studies," G.J. Handelman, D.M. Snodderly, N.I. Krinsky, M.D. Russett, and A.J. Alder, Invest. Ophthalmol. 1991, Vis. Sci. 32 (11 pages).

"Aging of the human lens," J. Pokorny, V.C. Smith, and M. Lutze, Appl., Opt. 26, 1987 (4 pages), November.

O.W. van Assendelft, *Spectroscopy of hemoglobin derivatives*, C.C. Thomas ed., (C.C. Thomas, Springfield, IL, 1979) (2 pages), December.

"Spectral reflectance of the human eye," D. van Norren and L. F. Tiemeijer, Vision Res. 1986, 26 (8 pages), December.

"Lutein and Zeaxanthin Measured Separately in the Living Human Retina with Fundus Reflectometry," Jan van de Kraats. Martijn J. Kanis, Stijn W. Genders, Dirk van Norren, Investigative Ophthalmology & Visual Science, vol. 49, No. 12, Dec. 2008 (6 pages).

PCT International Search Report for International Application No. PCT/US2013/063492 mailed Dec. 30, 2013 (4 pages).

PCT Written Opinion for International Application No. PCT/US2013/063492 mailed Dec. 30, 2014 (5 pages).

* cited by examiner

MACULAR PIGMENT MEASUREMENT DEVICE WITH DATA QUALITY INDEXING FEATURE

CROSS-REFERENCE AND CLAIM OF PRIORITY TO RELATED APPLICATION

This application claims the benefit of and priority to U.S. Provisional Patent Application No. 61/720,737, which was filed on Oct. 31, 2012, which is incorporated herein by reference in its entirety.

FIELD OF THE INVENTION

The present invention relates to a macular pigment optical density measurement instrument that measures characteristics of the patient's eye, such as macular pigment.

BACKGROUND OF THE INVENTION

The retina is the layer of nerve cells at the back of the eye, which convert light into nerve signals that are sent to the brain. In humans, and in other primates (but not in most other mammals, or other types of animals), the retina has a small yellowish area in the center of the field of vision. That yellowish area is called the "macula." It provides fine-resolution vision in the center of the visual field and is essential to good vision. People who suffer from macular degeneration often lose the ability to read, recognize faces, drive, or walk safely on unfamiliar routes.

The surrounding portions of the macula can only provide coarse resolution. This physiological feature limits and controls the number of nerve signals that the brain must rapidly process, to form coherent rapid-response vision, and it also helps limit and control the huge number of rod and cone receptors that the eye must continually regenerate and recycle, every day. Many people do not realize the retina can provide only coarse resolution, outside of a limited central area, because the eyes and the brain have developed an extraordinary ability to synthesize coherent vision from a combination of fine and coarse resolution. During that type of vision synthesis, the eye muscles cause the eyes to flit back and forth over a larger field of vision, pausing at each location for just an instant while the eye quickly "grabs" a fine-resolution image of a limited area. This process occurs so rapidly that a person does not notice it happening, and does not pay attention to how a complete visual image and impression is being assembled and updated from combinations of fine and coarse resolution images.

There is also a peculiar anatomic structure in the retinas of humans, which points out the difference between fine resolution (provided by the macula) and coarse resolution (provided by the remainder of the retina). In humans, the blood vessels that serve the retina actually sit in front of the retina, where they can block and interfere with incoming light, before the light reaches the retina. This is counter-intuitive, and one should wonder why the retina evolved with a physical handicap that literally gets in the way of good, clear vision. The answer is, in those parts of the retina, only coarse vision is being created, and blood vessels positioned in front of the retina do not interfere with that type of coarse vision. By contrast, in the macular region in the center of the retina, the blood vessels in front of the retina are lacking and supply is only from blood vessels present anywhere behind the layer of neurons with rod and cone receptors. This is consistent with the macula providing fine resolution vision, which would be blocked and hindered if the blood vessels were located in front of the neurons, in ways that would intercept and blocking portions of the incoming light.

"Retinal degeneration" is a descriptive term, which refers to and includes an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome, and various other eye disorders that lead to gradual degeneration of the macula (and possibly other parts of the retina) over a span of time. This is not an exclusive list, and other subclasses and categories also are known. For example, age-related macular degeneration is subdivided into wet and dry forms, depending on whether abnormal and disruptive blood vessel growth is occurring in the structural layers behind the retina.

The causes and effects of macular degeneration, and efforts to prevent or treat it, are described in numerous books (e.g., "Macular Degeneration," by Robert D'Amato et al (2000) and "Age-Related Macular Degeneration," by Jennifer Lim (2002)), articles ("Age-Related Macular Degeneration" by Berger et al (1999)) and patents, such as U.S. Pat. No. Re. 38,009, which is assigned to ZeaVision LLC, and is incorporated by reference in its entirety.

In recent years, awareness has grown, among some researchers but not among the general public, of the roles that macular pigment plays, in the health and longevity of the macula. Therefore, the two carotenoid pigments that create and provide the macular pigment are discussed below.

The Macular Pigments: Zeaxanthin and Lutein: The macula has a yellowish color because it contains unusually high concentrations of two specific pigments, called zeaxanthin and lutein. Both are carotenoids, similar to beta-carotene but with hydroxy groups coupled to their end rings (the presence of one or more oxygen atoms causes a carotenoid to be categorized as a "xanthophyll", so zeaxanthin and lutein are sometimes referred to as xanthophylls). Both of those two carotenoids are known to be protective and beneficial, in human retinas, by mechanisms that include: (1) absorption of destructive ultraviolet photons; and (2) quenching of destructive radicals. Both of those mechanisms, and other potential protective mechanisms, are discussed below.

In addition to their involvement in the macula and macular degeneration, zeaxanthin and lutein also are present in other eye structures (including the eye lens), and undesirably low levels of those two carotenoids appear to be correlated with higher risks of disorders such as cataracts. Accordingly, although the discussion herein focuses on macular degeneration, it should be recognized that any comments herein about macular pigment levels also have varying degrees of relevance to some other eye disorders as well. Similarly, any comments herein about macular degeneration should be recognized as including disorders that are referred to by other names (such as diabetic retinopathy, Stargardt's disease, etc.), but that involve or lead to gradual deterioration of the macula.

The structures of zeaxanthin and lutein are very similar because they are isomers of each other, differing only in the placement of a double bond in one end ring. In lutein, the ring with a "misplaced" double bond is called an "epsilon" ring.

All of the other end rings have "beta" ring structures, which refer to the sequence of double bonds found in beta-carotene's two end rings.

However, that single minor structural difference, between zeaxanthin versus lutein, has profound effects on the traits, performance, and tissue concentrations of those two different molecules, in both plants and animals. Briefly, the lutein molecule has a bend where the epsilon ring joins the "straight chain" segment between the two end rings. That bend, near one end, allows lutein to fit properly into ring-shaped "light-harvesting" structures, in the chloroplasts of plant cells. Since light-harvesting (which is part of photosynthesis) is crucial in plants, lutein evolved as a major and dominant carotenoid, in essentially all plants.

By contrast, zeaxanthin does not have a bend at either end. Since it is relatively straight, it cannot fit properly into the circular light-harvesting structures that help carry out photosynthesis, in plants. Therefore, it evolved in plants in ways that led to a very different role in a day-night cycle, in which zeaxanthin and a similar carotenoid called violaxanthin are converted back and forth into each other. As a result, zeaxanthin does not accumulate in substantial quantities in most types of plants (although a few exceptions are known, such as corn and red peppers). Even in dark green plants, such as spinach or kale, lutein content is dozens or even hundreds of times greater than zeaxanthin content. On an aggregate basis, the total amount of zeaxanthin in typical diets in industrial nations is believed to be about 1% (or possibly even less) of the total lutein supply.

Another important difference between zeaxanthin and lutein is that zeaxanthin has a longer and more protective "conjugated cloud" of electrons surrounding it, compared to lutein. When a series of carbon atoms are bonded to each other by alternating double and single bonds, the electrons become mobile, and are no longer affixed to specific bond locations. Those electrons form a flexible and movable electron "cloud". This same type of cloud also appears in benzene rings and other "aromatic" organic compounds, and it is well-known to chemists.

That type of flexible and movable electron cloud is ideally suited for absorbing high-energy radiation (in the ultraviolet, near-ultraviolet, and deep blue part of the spectrum), without suffering damage or breakage of the molecule. In addition, a flexible and movable electron cloud is ideally suited for neutralizing and "quenching" oxygen radicals, which are aggressively unstable and destructive molecules, containing oxygen atoms having unpaired electrons. Oxidative radicals are important damaging agents in any cells and tissues that are being bombarded by high levels of UV radiation, since UV radiation often breaks bonds that involve oxygen atoms, in ways that create unpaired electrons where the broken bonds previously existed.

All carotenoids are assembled, in plants, from a 5-carbon precursor called isoprene, which has two double bonds separated by a single bond. As a result, all carotenoids have at least some sequence of alternating double and single bonds, leading to a conjugated electron cloud covering at least part of the carotenoid molecule. This is a basic and shared trait of all carotenoids, and it explains how carotenoids provide two crucial benefits (i.e., absorption of UV radiation, and quenching of destructive radicals) that are vital to plants, which must often sit in direct sunlight for hours each day.

However, different carotenoids have conjugated electron clouds that different lengths, and different potencies and protective traits. In particular, there is a crucial difference between the conjugated electron clouds of zeaxanthin and lutein. The placement of the double bonds in both of zeaxanthin's two end rings continues and extends the pattern of alternating double and single bonds, from the straight chain. This extends zeaxanthin's conjugated and protective electron cloud, out over a part of both of zeaxanthin's two end rings.

By contrast, the position of the double bond in lutein's "epsilon" ring disrupts the alternating double/single bond sequence, established by the straight-chain portion of the molecule. This disrupts and terminates the conjugated electron cloud, and it prevents the protective, UV-absorbing, radical-quenching electron cloud from covering any part of lutein's epsilon end ring. That structural difference in their end rings becomes highly important, because zeaxanthin and lutein are deposited into animal cells in ways that cause them to "span" or "straddle" the outer membranes of the cells. It causes zeaxanthin and lutein to be deposited into animal cell membranes in a way that places them perpendicular to the surfaces of the membrane that surrounds and encloses a cell.

It is not fully known, at a molecular level, how lutein's lack of symmetry, and lack of a protective conjugated electron cloud over one end ring, affect its deposition in cells in the human macula. For example, it is not known whether the protective beta rings at one end of lutein are consistently or predominantly placed on either the external or internal surfaces of cell membranes. In addition, it is not known whether lutein is consistently deposited, into human cell membranes, in a membrane-spanning orientation.

However, other aspects of zeaxanthin and lutein content and deposition in blood, and in the macular regions of human retinas, are well-known. Despite the rarity of zeaxanthin in food sources (as mentioned above, zeaxanthin content in typical diets is believed to be less than about 1% of the lutein supply), zeaxanthin concentrations in human blood average about 20% of lutein levels. This clearly indicates that the human body does something that indicates a selective preference for zeaxanthin, over lutein.

Even more revealingly, zeaxanthin is even more concentrated in the crucially important center of the human macula, which provides fine-resolution vision in humans. In the crucially important center of a healthy human macula, zeaxanthin is present at levels that average more than twice the concentrations of lutein. By contrast, lutein is present in higher levels around the less-important periphery of the macula. While the mechanisms which create that pattern of deposition are not fully understood, it recently has been reported that certain enzymes that appear to be involved will clearly bind to zeaxanthin with relatively high affinity under in vitro conditions; however, those same enzymes will not bind to lutein with any substantial affinity (Bhosale et al 2004).

Accordingly, these differences in how zeaxanthin and lutein are deposited in the macula provide strong evidence that the macula wants and needs zeaxanthin, more than lutein. The patterns of deposition, and the known structural and electron cloud differences, suggest and indicate that the macula wants and needs zeaxanthin, and it uses lutein only if and when it cannot get enough zeaxanthin.

This belief is also supported by another important finding. The macula may attempt to convert lutein into zeaxanthin. However, the conversion process cannot convert lutein into the normal stereoisomer of zeaxanthin found in plants and in the diet (the 3R,3'R stereoisomer). Instead, it converts lutein into a different stereoisomer that has never been found in any food sources or mammalian blood. That non-dietary isomer has one end ring with the conventional "R" configuration; however, the second end ring has an unnatural "S" configuration that is never found in the normal diet. That S-R isomer (and R-S isomer) is called meso-zeaxanthin.

Consequently, while lutein may have benefits, a growing body of knowledge and evidence indicates that zeaxanthin is the ideal carotenoid for helping prevent and treat the class of eye diseases that fall into the category of retinal degeneration.

To address problems associated with retinal degeneration in a patient, instruments are needed to help measure the macular pigment within the patient's eye. While various instruments exist that can perform this function, improvements are needed to provide instruments that are more accurate, easier to use, and less time consuming. For example, many instruments require the taking of multiple measurements from a patient and some or all of the data may not be accurate such that a re-test is needed.

The present invention is directed to an improved instrument that can help to automatically determine whether the data captured by the instrument is acceptable for providing proper results. If it is, the instrument instructs the operator that the data is acceptable. If the data is not acceptable, the instrument instructs the operator to take new data from the patient.

SUMMARY OF THE INVENTION

According to one aspect of the present invention, a system measures macular pigment of a macula of a human eye of a user. The system comprises a light source having a first light and a second light that modulate at variable frequencies, an input device for receiving an input indicating the frequency at which the user perceives the modulation of the first light and a second light, a display device, at least one processor, and one or more memory devices. The one or more memory devices storing instructions that, when executed by at least one processor, cause the system to (i) display, on the display device, test data corresponding to the user's inputs from the input device, (ii) determine whether the test data are valid or invalid through a curve-fitting algorithm, (iii) automatically indicate that the test data are valid or invalid.

According to another aspect of the present invention, a method of using a measurement system for measuring a macular pigment of an eye of a subject, comprising: (i) receiving input data from a subject corresponding to when the subject perceives a flicker in two lights; and (ii) displaying the input data in a manner that automatically indicates whether the input data is valid or invalid.

Additional aspects of the invention will be apparent to those of ordinary skill in the art in view of the detailed description of various embodiments, which is made with reference to the drawings, a brief description of which is provided below.

DETAILED DESCRIPTION

Figure 1:
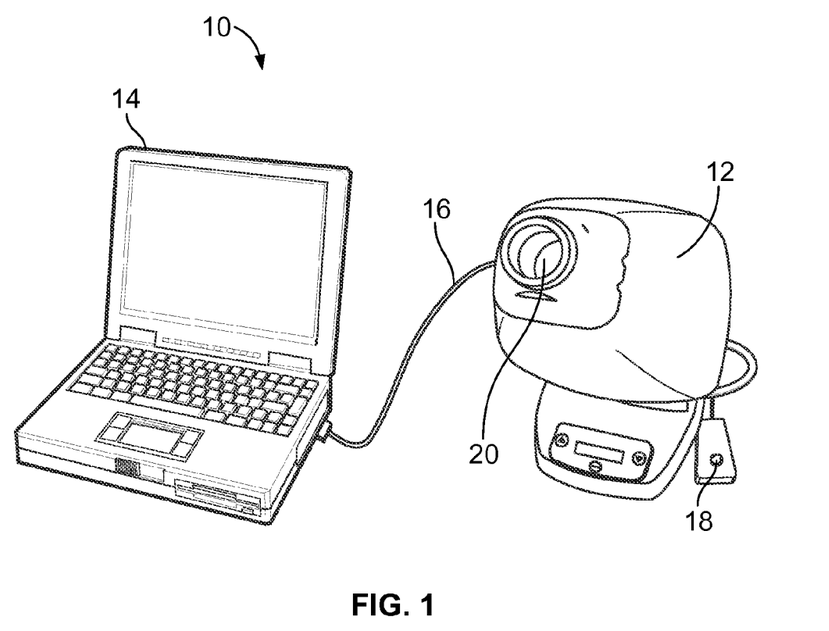
FIG. 1 is a system for measuring macular pigment including a measurement device and a computer with a display.

FIG. 1 illustrates a MPOD detection system 10 that includes a heterochromatic flicker photometry (HFP) instrument 12 and a computer 14 for providing inputs and viewing outputs on its display. The HFP instrument 12 is typically electronically coupled to the computer 14 via a wire connection 16, although a wireless connection is possible as well. As shown, the HFP instrument 12 is a commercially available from ZeaVision LLC, Chesterfield, Mo., and is sold under the trademark QuantifEYE®.

The HFP instrument 12 includes an input device 18 allowing a test subject to provide an input when he or she perceives a flicker during the test. Generally, the HFP instrument 12 has a target arranged to be viewed by the test subject with one eye (left or right) through the viewing window 20. The target includes a blue light and a green light arranged to undergo a modulation in opposing phases. The modulation decreases from an initial modulation frequency at which an initial flicker of the first light and second light is not perceivable by the test subject (e.g., decreased at a rate of between 3 Hz per second and 7 Hz per second). The test subject inputs a response from the input device 18 to indicate when he or she perceives the flicker. The modulation frequency at which the test subject can perceive the flicker provides a first data point that is later used to provide a correlation to an MPOD value for that patient.

The ratio of the blue light and the green light for the target is then changed (e.g., increased blue light and decreased green light) for the next data point. The frequency modulation decreases from an initial modulation frequency at which an initial flicker of the first light and second light is not perceivable by the test subject, to a point at which the test subject perceives the flicker. The test subject again indicates, via the input device 18, the frequency at which he or she can perceive the flicker. This is a second data point. The process continues at different relative values (ratios) of blue light and green light to create multiple data points.

Figure 2:
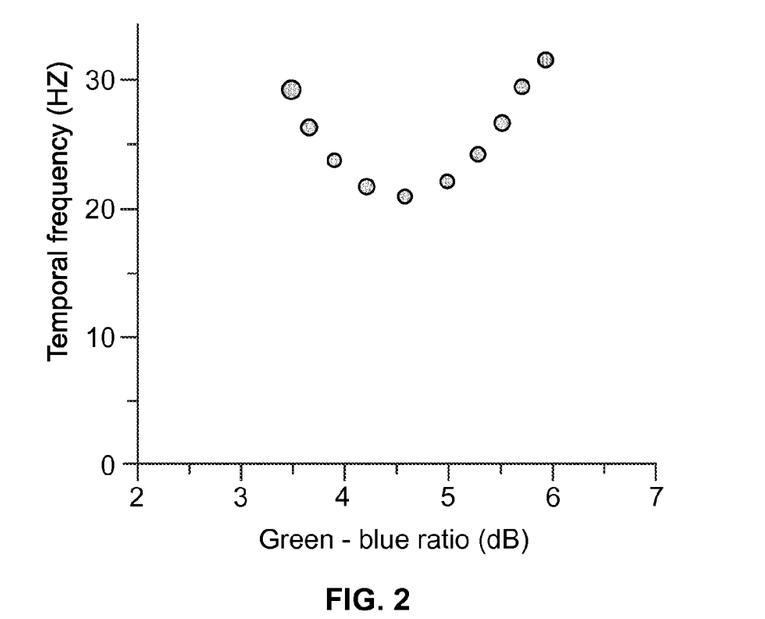
FIG. 2 is a graph of the user inputs from the system of FIG. 1.

FIG. 2 illustrates a graph of the data derived from the test for a typical test subject. Each of the ten data points on FIG. 2 represents the test subject's input on the input device 18 for ten different test conditions having different ratios of green light to blue light (measured in decibels "dB" along the x-axis). The modulation frequency on the y-axis is the flicker rate for the target, and each data point represents a corresponding flicker rate at which the test subject began to perceive a flicker. The HFP instrument 12 and its procedures are described in U.S. Pat. No. 7,390,090, which is hereby incorporated by reference in its entirety. Additionally, alternative procedures for using the HFP instrument 12 are described in an article entitled "*A New Desktop Instrument for Measuring Macular Pigment Optical Density Based on a Novel Technique For Setting Flicker Thresholds*." Ophthalmic & Physiological Optics. 29(2):127-137, March 2009, by van der Veen, Rob L. P.; Berendschot, Tos T. J. M.; Hendrikse, Fred; Carden, David; Makridaki, Maria; Murray, Ian J, which is also hereby incorporated by reference in its entirety.

Because the HFP instrument 12 relies on the test subject inputs via the input device 18, there can be a tendency for errors when macular pigment density is being measured. The test subject must fixate on a target or stimulus that will change (i.e., the target will begin to flicker at different rates). While some test subjects readily understand the operating instructions and take the test appropriately, others test subjects have difficulty understanding and following instructions and, therefore, their macular pigment measurement is inaccurate. A test subject may anticipate the change in frequency and respond via the input device too early when they perceive no flicker. The test subject may blink multiple times for eye comfort and/or clarity at a critical point in the test at which the frequency is being decreased and becomes perceptible to the test subject, but he or she misses it due to blinking. The patient may simply have problems hitting the input device properly, or be distracted during a few data pints in the test. When these test subject errors are introduced into the system, the smooth curve in FIG. 2 (which is good for ultimately measuring the MPOD value) can be replaced by scattered data that is not as useful for measuring data, or is entirely inaccurate at providing the test subject's MPOD value.

Further, when the test subject begins providing bad data, the operator (e.g., an assistant in an eye care practice) may not catch the errors when looking at a graph like FIG. 2 on the display of the computer 14. Operator interpretation/assessment of each test subject's graph must be taught to instrument operators. The teachings would include graph trend line shape, alignment of responses as "points on the graph" to the trend line, and reaching predefined minimum or macular pigment saturation. While well trained instrument operators can interpret the results of the HFP instrument 12 on the computer 14 accurately, employee turnover in eye care practices is common and utilization of the instrument may not be so intuitive to new test subjects.

The present invention seeks to overcome the aforementioned problems of the MPOD detection system 10 by providing an automatic data quality index. The data quality index (DQI) may utilize one or more curve-fitting algorithms to ensure the data from the test subject is accurate. Based on the results of the curve-fitting algorithm, the display of the computer 14 can provide the operators and the test subject with an indication of whether the data was accurate (i.e., acceptable) or, if a retest is needed. These types of outputs on the display of the computer 14 are shown in with respect to FIGS. 3-5.

Figure 3:
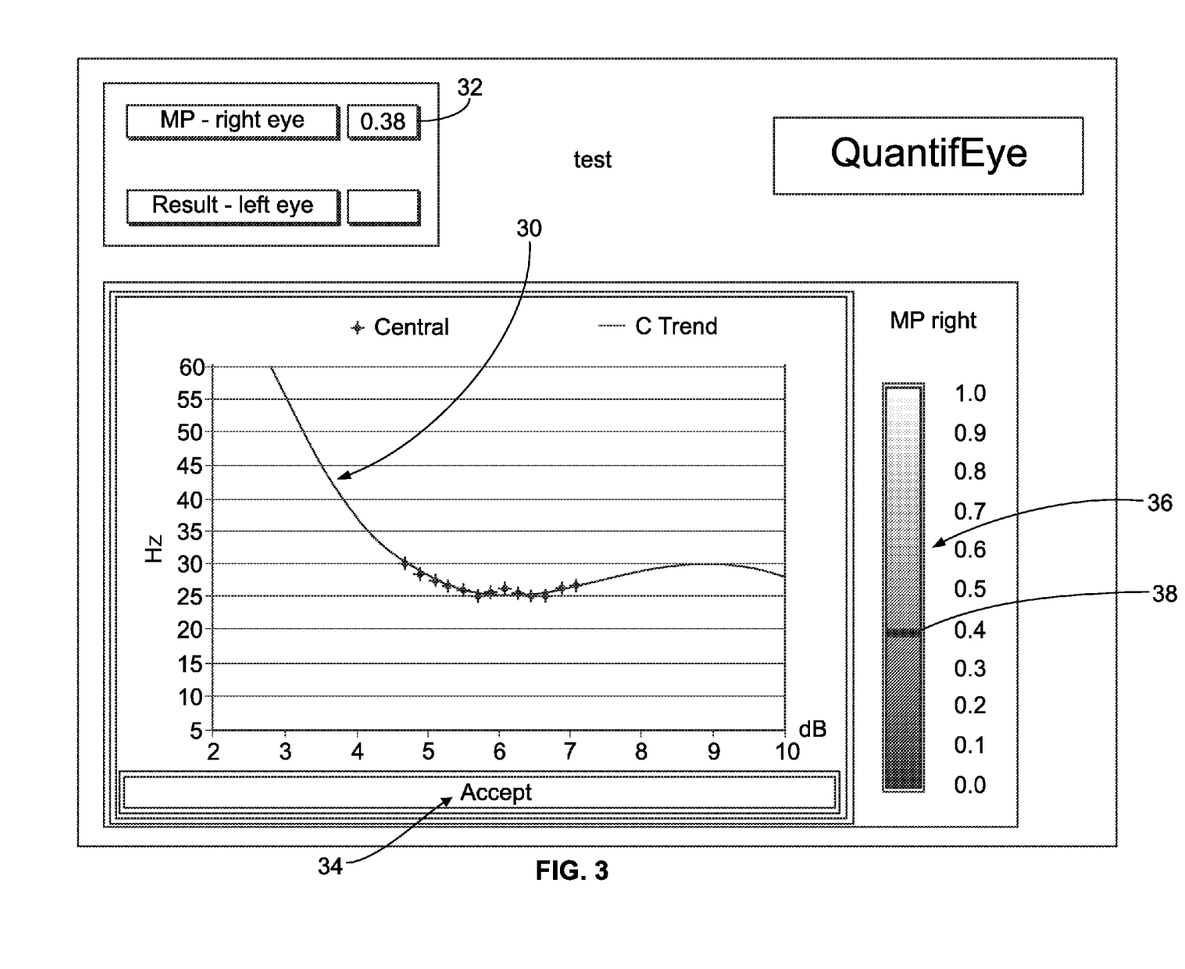
FIG. 3 illustrates the display of the data inputs from the system of FIG. 1 when the data are acceptable.

In FIG. 3, the curve-fitting algorithm has been used to develop a curve 30 that best matches the test subject's data. The curve-fitting algorithm may be a polynomial-curve fitting algorithm, such as the least squares methodology, which is known in the art. Based on how well the curve fits the data, the DQI is established to provide the test subject and operator with an indication of whether the test data is accurate enough to determine the patient's MP (Macular Pigment) value. In FIG. 3, the MP display field 32 is shown above the graph and its MP value for the test subject is 0.38. Additionally, a MP bar-graph 36 is scaled from 0.0 to 1.0 on the right side of the graph and provides a visual indicator 38. Here, the visual indicator 38 is also indicating a MP value of 0.38, just as show in the MP display field 32. Because the MP value of 0.38 is above a predetermined threshold value for the MP (e.g., 0.2), the operator and test subject understand the patient's MP value is acceptable. More importantly, the curve-fitting process for the curve 30 automatically determines the accuracy and acceptability of the data, as indicated by the "Accept" in the message field 34 appearing below the graph. Thus, the test for the right eye is complete. The left eye may now be tested in a similar manner.

The message field 34 is preferably color-coded to indicate the data's acceptability. A green, yellow or red region on the DQI message 34 indicates to accept data, to accept data with caution and retesting may yield better results, or to reject the score because it is inaccurate. Alternatively, instead of the 3-color-code scheme in the DQI message field 34, (e.g., Red, Yellow and Green), a 2-color-code scheme may exist to make it clear when to re-test.

Figure 4:
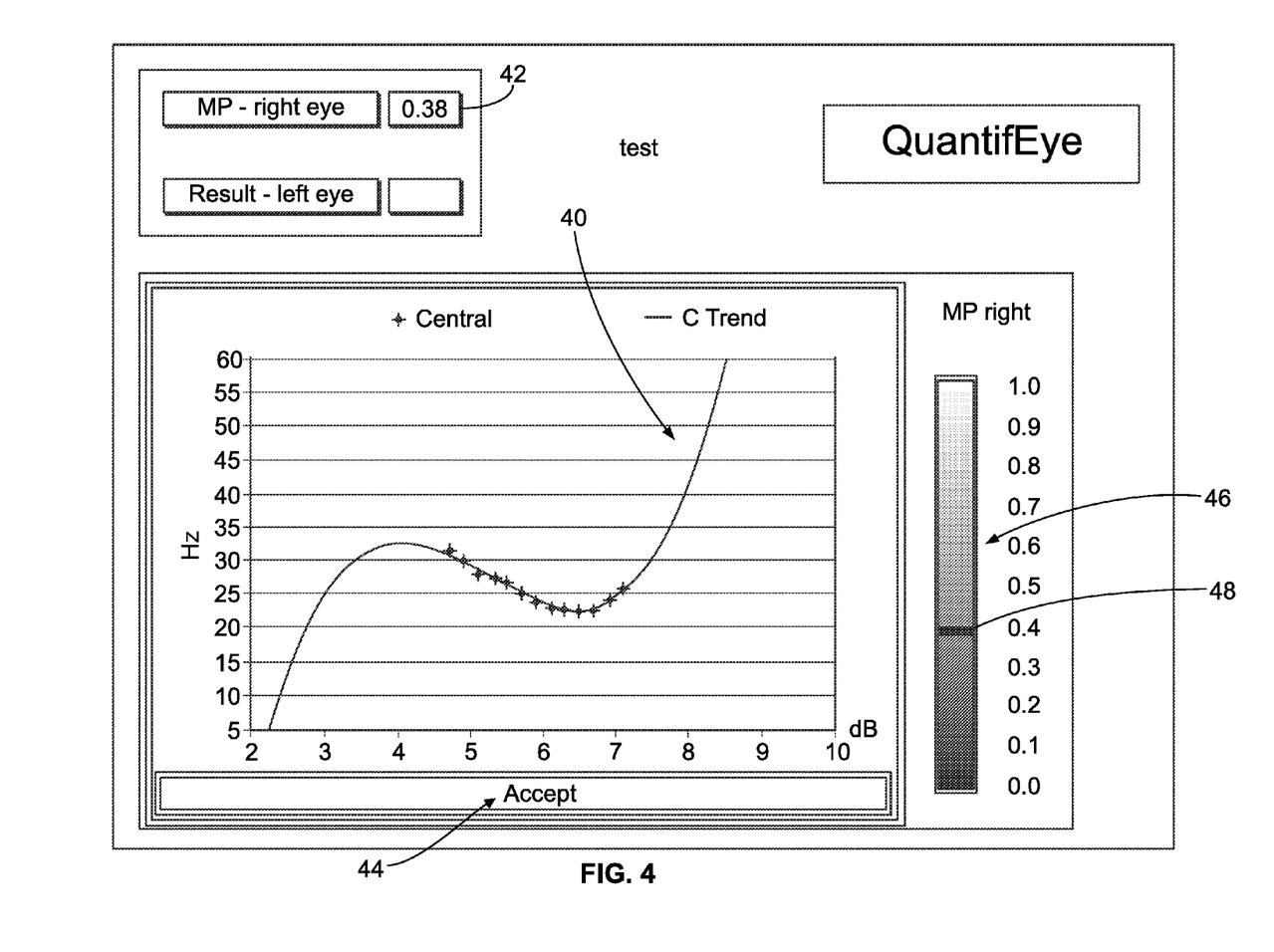
FIG. 4 illustrates the display of a second set of data inputs from the system of FIG. 1 when the data are acceptable.

In FIG. 4, the curve-fitting algorithm has been used to develop another curve 40 that best matches another test subject's data. The MP value field 42 is shown above the graph and its value for the test subject is again 0.38 (coincidentally the same as in FIG. 3, although it surely could be different). The message field 44 includes an "Accept" message to indicate the curve 40 fit the data well enough and, thus, the data was accurate.

Figure 5:
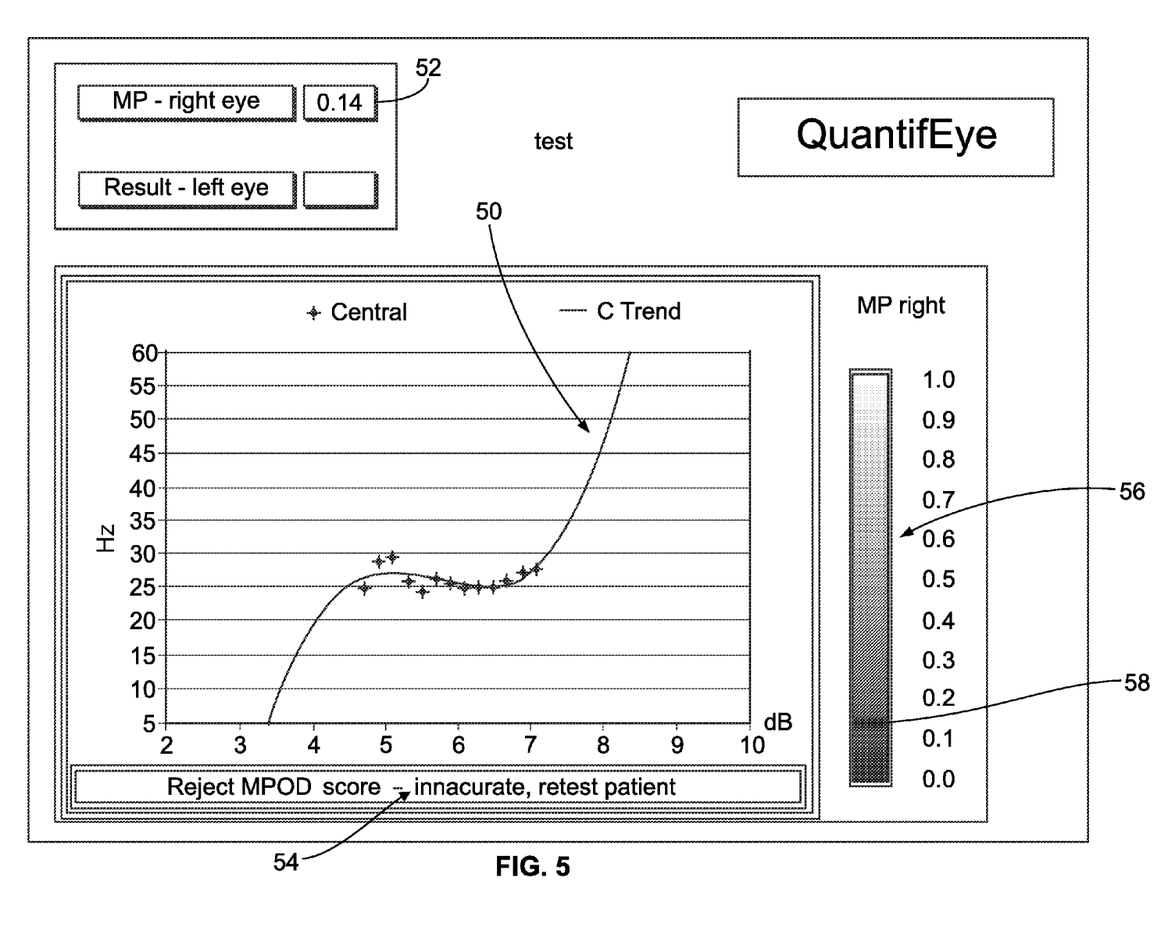
FIG. 5 illustrates the display of a third set of data inputs from the system of FIG. 1 when the data are unacceptable.

In FIG. 5, the curve-fitting algorithm has been used to develop another curve 50 that best matches yet another test subject's data. In FIG. 5, the MP display field 52 has a value of 0.14, which is relatively low suggesting the patient has a lower amount of macular pigment. The MP bar-graph 56, which is scaled from 0.0 to 1.0 on the right side of the graph, also provides a visual indicator 58 of the MP value at 0.14. However, this test subject's data is unacceptable, as indicated by the "Inaccurate, Retest Patient" message in the DQI message field 54 appearing below the graph. Thus, the low MP value may have something to do with the testing itself, and not the patient's macula. This subject should be re-tested.

The test can include both central macula data and peripheral macula data, as disclosed in the aforementioned article and U.S. Pat. No. 7,390,090, which have been incorporated by reference. Curves for both types of data can be displayed at the same time (i.e., two curves in the display screen). And, data problems can be assumed (and a retest is needed) when the two curves have certain overlapping characteristics.

When the test data is accurate, the test data is used to correlate to the patient's MPOD through logarithmic functions, which are taught by the aforementioned article and/or U.S. Pat. No. 7,390,090. This MP value is a dimensionless value (e.g., 0.0 to 1.0 as shown in the MP bar graphs 36, 46, and 56 in FIGS. 3-5) indicative of the amount of pigment located at the macula. It should be noted that the MPOD as measured by one form of instrument, such as the system 10, may be different from the MPOD measured by another form of MPOD-measuring instrument (e.g. reflectometer). Nevertheless, the skilled artisan will recognize that correlations can be developed between the MPOD values of a first type of instrument and the MPOD values of a second type of instrument.

If a patient's MPOD value is determined to be low, zeaxanthin and/or lutein supplementation may be recommended to increase the patient's macular pigment. By conducting follow-up periodic testing of the patient, the effects of supplementation should become noticeable. Zeaxanthin supplementation can be in the form of daily tablets or capsules, such as those supplements sold by ZeaVision LLC of Chesterfield, Mo.

Each of these embodiments and obvious variations thereof is contemplated as falling within the spirit and scope of the claimed invention, which is set forth in the following claims.

The invention claimed is:

1. A measurement system for measuring macular pigment from an eye of a subject, comprising:
   a light source having a first light and a second light that modulates at variable frequencies;
   an input device for receiving an input indicating the frequency at which the user perceives the modulation of the first light and a second light;
   a display device;
   at least one processor; and one or more memory devices storing instructions that, when executed by at least one processor, cause the system to:
   display, on the display device, test data corresponding to the user's inputs from the input device,
   determine whether the test data are valid or invalid through a curve-fitting algorithm,
   automatically indicate that the test data are valid or invalid.

2. The system of claim 1, wherein the modulation decreases until reaching the modulation frequency at which the user indicates that he or she perceives the modulation.

3. The system of claim 1, wherein the modulation frequency at which the user provides an input is between about 15 Hz and about 35 Hz.

4. The system of claim 1, wherein the first light is blue and the second light is green.

5. The system of claim 1, wherein the display device further displays the curve that is fitted to the test data.

6. The system of claim 1, wherein the instructions cause the system to display, on the display device, a macular-pigment value indicative of the amount of the patient's macular pigment.

7. The system of claim 6, wherein the macular-pigment value is displayed on a scaled bar graph.

8. The system of claim 1, wherein the display device provides the automatic indication of whether the test results are valid or invalid.

9. The system of claim 8, wherein the automatic indication includes a message field providing a message.

10. The system of claim 8, wherein the automatic indication includes the use of at least two colors, a first color indicating the test data is valid, a second color indicating the test data is invalid.

11. A measurement system for measuring macular pigment from an eye of a subject, comprising:
   a light source arranged to be viewed by the subject, the light source comprising a first light and a second light arranged to undergo a modulation in opposing phases, the modulation decreasing from an initial modulation frequency at which an initial flicker of the first light and second light is not perceivable by the subject, the light source capable of providing a plurality of different ratios of the amount of the first light relative to the second light;
   an input device for receiving inputs from the subject to indicate when he or she perceives a flicker in the light source; and
   a display device for displaying (i) test data points corresponding to the user's inputs at the plurality of different ratios of the amount of the first light relative to the second light and (ii) an automatic indication of whether the test data is acceptable or unacceptable.

12. The system of claim 11, wherein the decreasing of the modulation frequency is stopped when the user provides an input indicating that the flicker is perceived.

13. The system of claim 11, wherein the modulation frequency is decreased at a rate of between 3 Hz per second and 7 Hz per second.

14. The system of claim 11, wherein the display device displays a macular-pigment value for the subject in a scaled bar graph.

15. The system of claim 11, wherein the automatic indication includes a message field providing a message.

16. The system of claim 11, wherein the automatic indication includes the use of at least two colors, a first color indicating the test data is valid, a second color indicating the test data is invalid.

17. The system of claim 11 , wherein the display device further includes a curve that is fitted to test data.

18. The system of claim 11, wherein the first light is blue and the second light is green.

* * * * *